(12) United States Patent
Bittner et al.

(10) Patent No.: US 8,465,668 B2
(45) Date of Patent: Jun. 18, 2013

(54) SURFACTANTS WITH A POLYETHERSULFONATE STRUCTURE METHOD FOR PRODUCTION THEREOF AND USE THEREOF FOR TERTIARY CRUDE OIL PRODUCTION

(75) Inventors: Christian Bittner, Bensheim (DE);
Oetter Günter, Frankenthal (DE);
Ulrich Steinbrenner, Neustadt (DE);
Jürgen Huff, Ludwidshafen (DE);
Marcus Guzmann, Mühlhausen (DE)

(73) Assignee: BASF SE (DE)

( * ) Notice: Subject to any disclaimer, the term of this patent is extended or adjusted under 35 U.S.C. 154(b) by 680 days.

(21) Appl. No.: 12/738,236

(22) PCT Filed: Oct. 15, 2008

(86) PCT No.: PCT/EP2008/063834
§ 371 (c)(1),
(2), (4) Date: Apr. 15, 2010

(87) PCT Pub. No.: WO2009/050179
PCT Pub. Date: Apr. 23, 2009

(65) Prior Publication Data
US 2010/0213409 A1    Aug. 26, 2010

(30) Foreign Application Priority Data
Oct. 16, 2007  (EP) .................................. 07118547

(51) Int. Cl.
*C09K 3/00*       (2006.01)
*C07C 309/04*     (2006.01)
*C07C 309/09*     (2006.01)
*C07C 309/17*     (2006.01)
*C11D 17/00*      (2006.01)

(52) U.S. Cl.
USPC ...... 252/182.12; 562/108; 562/109; 562/110; 562/111; 510/127; 507/936; 8/150.5

(58) Field of Classification Search
USPC ................... 252/182.12; 562/108, 109, 110, 562/111; 510/127
See application file for complete search history.

(56) References Cited

U.S. PATENT DOCUMENTS

| | | | |
|---|---|---|---|
| 2,308,841 A * | 1/1943 | Werntz .......................... | 562/109 |
| 3,268,563 A | 8/1966 | Shen et al. | |
| 3,508,621 A | 4/1970 | Gaylord et al. | |
| 3,811,504 A | 5/1974 | Flournoy et al. | |
| 3,811,505 A | 5/1974 | Flournoy et al. | |
| 3,811,507 A | 5/1974 | Flournoy et al. | |
| 3,890,239 A | 6/1975 | Dycus et al. | |
| 4,077,471 A | 3/1978 | Shupe et al. | |
| 4,978,780 A | 12/1990 | Fikentscher et al. | |
| 4,987,249 A | 1/1991 | Sandler | |
| 5,015,414 A * | 5/1991 | Kamegai et al. ............. | 510/127 |
| 5,025,104 A * | 6/1991 | Sandler ........................ | 562/109 |
| 5,310,508 A * | 5/1994 | Subramanyam et al. ..... | 510/127 |
| 5,430,180 A | 7/1995 | Sandler | |

FOREIGN PATENT DOCUMENTS

| | | |
|---|---|---|
| DE | 3918265 | 1/1991 |
| DE | 4325237 A1 | 2/1995 |
| DE | 10243361 A1 | 4/2004 |
| EP | 003183 | 7/1979 |
| EP | 0207312 | 1/1987 |
| EP | 0353469 | 2/1990 |
| GB | 2143563 | 2/1985 |
| WO | WO-2006/131541 A1 | 12/2006 |

OTHER PUBLICATIONS

International Preliminary Report on Patentability for PCT/EP2008/063834, issued Apr. 20, 2010.

* cited by examiner

*Primary Examiner* — Peter F Godenschwager
(74) *Attorney, Agent, or Firm* — Novak Druce Connolly Bove + Quigg LLP

(57) ABSTRACT

Surfactants with polyether sulfonate structure, which have a propanonylsulfonic acid group as a head group, a process for preparing such surfactants and their use for tertiary mineral oil extraction.

26 Claims, 2 Drawing Sheets

(A)

(B)

Figure 1:
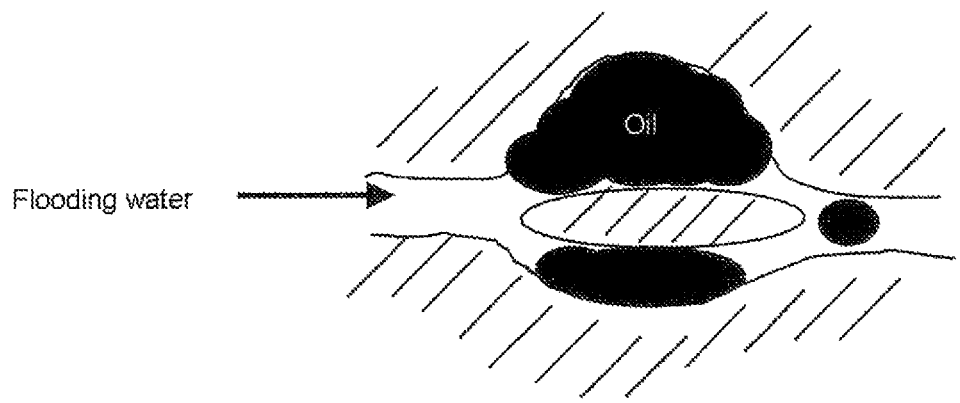

SURFACTANTS WITH A POLYETHERSULFONATE STRUCTURE METHOD FOR PRODUCTION THEREOF AND USE THEREOF FOR TERTIARY CRUDE OIL PRODUCTION

CROSS REFERENCE TO RELATED APPLICATIONS

This application is a national stage application under 35 U.S.C. §371 of PCT/EP2008/063834, filed Oct. 15, 2008, which claims benefit to European application 07118547.4, filed Oct. 16, 2007, the entire disclosures of which are hereby incorporated by reference.

The present invention relates to novel surfactants with polyether sulfonate structure, which have a propanonylsulfonic acid group as a head group, to a process for preparing such surfactants and to their use for tertiary mineral oil extraction.

In natural mineral oil deposits, mineral oil is present in the cavities of porous reservoir rocks which are sealed toward the surface of the earth by impermeable top layers. The cavities may be very fine cavities, capillaries, pores or the like. Fine pore necks may, for example, have a diameter of only approx. 1 µm. As well as mineral oil, including fractions of natural gas, a deposit comprises water with a greater or lesser salt content. The salt content of deposit water is not rarely from 5 to 20% by weight; but there are also deposits with a salt content of up to 27% by weight. The dissolved salts may, for example, be alkali metal salts; in some deposits, the deposit water, however, also comprises relatively high contents of alkaline earth metal ions, for example up to 5% by weight of calcium ions and/or magnesium ions.

In mineral oil extraction, a distinction is drawn between primary, secondary and tertiary extraction.

In primary extraction, the mineral oil flows, after commencement of drilling of the deposit, of its own accord through the borehole to the surface owing to the autogenous pressure of the deposit. The autogenous pressure can be caused, for example, by gases present in the deposit, such as methane, ethane or propane. By means of the primary extraction, according to the deposit type, it is, though, usually possible to extract only approx. 5 to 10% of the amount of mineral oil present in the deposit; thereafter, the autogenous pressure is no longer sufficient for extraction.

After primary extraction, secondary extraction is therefore used. In secondary extraction, in addition to the boreholes which serve for the extraction of the mineral oil, the so-called production bores, further boreholes are drilled into the mineral oil-bearing formation. Water is injected into the deposit through these so-called injection bores in order to maintain the pressure or to increase it again. As a result of the injection of the water, the mineral oil is forced through the cavities in the formation slowly, proceeding from the injection bore, in the direction of the production bore. However, this only works for as long as the cavities are completely filled with oil and the more viscose oil is pushed onward by the water (see FIG. 1). As soon as the mobile water breaks through cavities, it flows on the path of least resistance from this time, i.e. through the channel formed, and no longer pushes the oil onward. This situation is shown in FIG. 2: owing to the different polarity of oil and water, a high interface energy or interface tension arises between the two components. The two therefore adopt the smallest contact area, which results in a spherical oil droplet which no longer fits through the fine capillaries. At the end of the water flow, the oil is thus trapped in the capillaries in discontinuous form (isolated spherical droplets).

By means of primary and secondary extraction, generally only approx. 30 to 35% of the amount of mineral oil present in the deposit can be extracted.

It is known that the mineral oil yield can be enhanced further by measures for tertiary oil extraction. A review of tertiary oil extraction can be found, for example, in the Journal of Petroleum Science and Engineering 19 (1998) 265-280. Tertiary oil extraction includes, for example, thermal methods in which hot water or steam is injected into the deposit. This lowers the viscosity of the oil. The flow medium used may also be gases such as $CO_2$ or nitrogen.

Tertiary mineral oil extraction also includes methods in which suitable chemicals are used as assistants for oil extraction. These can be used to influence the situation toward the end of the water flow and as a result also to extract mineral oil hitherto held firmly within the rock formation.

Viscous and, capillary forces act on the mineral oil which is trapped in the pores of the deposit rock toward the end of the secondary extraction, the ratio of these two forces relative to one another being determined by the microscopic oil separation. By means of a dimensionless parameter, the so-called capillary number, the action of these forces is described. It is the ratio of the viscosity forces (velocity×viscosity of the forcing phase) to the capillary forces (interface tension between oil and water×wetting of the rock):

$$N_c = \frac{\mu v}{\sigma \cos\theta}.$$

In this formula, $\mu$ is the viscosity of the fluid mobilizing mineral oil, $v$ is the Darcy velocity (flow per unit area), $\sigma$ is the interface tension between liquid mobilizing mineral oil and mineral oil, and $\theta$ is the contact angle between mineral oil and the rock (C. Melrose, C. F. Brandner, J. Canadian Petr. Techn. 58, October-December, 1974). The higher the capillary number, the greater the mobilization of the oil and hence also the degree of oil removal.

It is known to those skilled in the art that the capillarity number toward the end of secondary mineral oil extraction is in the region of about $10^{-6}$ and that it is necessary to increase the capillarity number to from about $10^{-3}$ to $10^{-2}$ in order to be able to mobilize additional mineral oil. To this end, for example, the interface tension a between mineral oil and aqueous phase can be lowered by the addition of suitable surfactants. This technique is also known as "surfactant flooding". Suitable surfactants for surfactant flooding are especially surfactants which can lower $\sigma$ to values of $<10^{-2}$ mN/m (ultralow interfacial tension). In this manner, it is possible to change the shape of the oil droplets and to force them through the capillary orifices by means of the flowing water.

It is desired that the oil droplets subsequently combine to a continuous oil bank. This is shown schematically in FIG. 3. The formation of a continuous oil bank has two kinds of advantages: firstly, as the continuous oil bank advances through new porous rock, the oil droplets present there can merge with the bank. Moreover, the combination of the oil droplets to form an oil bank significantly reduces the oil-water interface, and surfactant which is no longer required is thus released. The released surfactant can then mobilize oil droplets remaining in the formation. This is shown schematically in FIG. 4. An ultralow interface tension between the water phase and the oil phase is also required to combine the oil droplets to an oil bank and to incorporate new oil droplets into the oil bank. Otherwise, individual oil droplets remain or are not incorporated into the oil bank. This reduces the efficiency of the surfactant flooding.

In general, after the surfactant flooding, to maintain the pressure, water is not injected into the formation, but rather a higher-viscosity aqueous solution of a polymer with high thickening action. This technique is known as "polymer flooding".

In surfactant flooding, the surfactants should form a microemulsion (Winsor type III) with the water phase and the oil phase. A microemulsion (Winsor type III) is not an emulsion with particularly small droplets, but rather a thermodynamically stable, liquid mixture of water, oil and surfactants which has a very low interface tension and usually possesses a low viscosity. It is in equilibrium with excess water and excess oil. A low viscosity is desirable to transport the emulsion in the mineral oil formation. At an excessively high viscosity of the phase to be transported, a very high pressure would have to be applied in the course of polymer flooding. This is firstly expensive, but there is in particular also the risk that the pressure might undesirably blast new cavities in the mineral oil formation. In addition, a combination of the mobilized oil droplets to a continuous oil bank is hindered in the case of excessively high viscosities.

The requirements on surfactants for tertiary mineral oil extraction differ significantly from the requirements on surfactants for other applications.

The surfactants should reduce the interface tension between water and oil (typically approx. 20 mN/m) to particularly low values of less than $10^{-2}$ mN/m, in order to enable sufficient mobilization of the mineral oil. This has to be done at the customary deposit temperatures of from approx. 30 to approx. 130° C. and in the presence of water with a high salt content, especially also in the presence of high contents of calcium and/or magnesium ions; the surfactants must thus also be soluble in deposit water with a high salt content. The temperature window within which a microemulsion forms should at the same time be very wide. To prevent surfactant losses in the formation, the surfactants should have a low tendency to form viscous or large surfactant superstructures, and have a low adsorption capacity. Moreover, the surfactants should have a high chemical stability under the conditions existing in the formation. This includes in particular a high long-term stability: the migration velocity of the surfactant flood in the formation is often less than 1 m/day. According to the distance between injection bore and extraction bore, the residence times of the surfactant in the mineral oil deposit may be several months.

For use in the tertiary mineral oil extraction, various polyether sulfonates have already been proposed.

U.S. Pat. No. 3,811,505 discloses a mixture of an anionic surfactant and a nonionic surfactant for use in deposits whose deposit water comprises from 0.5 to 0.9% by weight of polyvalent ions. The anionic surfactants are alkyl sulfonates or alkyl phosphates having in each case from 5 to 25 carbon atoms, alkylaryl sulfonates or alkylaryl sulfonates whose alkyl radical has in each case from 5 to 25 carbon atoms. The nonionic surfactants are polyethoxylated alkylphenols which have from 6 to 20 ethoxy groups and whose alkyl radical has from 5 to 20 carbon atoms, or polyethoxylated aliphatic alcohols having from 6 to 20 carbon atoms and from 6 to 20 ethoxy groups.

U.S. Pat. No. 3,811,504 discloses a mixture of 2 different anionic surfactants and a nonionic surfactant for use in deposits whose deposit water comprises from 0.15 to 1.2% calcium and magnesium ions. The former anionic surfactant comprises alkyl or alkylaryl sulfonates, the second comprises alkyl polyethoxy sulfates, and the nonionic surfactant comprises polyethoxylated aliphatic or aromatic alcohols. Surfactant mixtures of similar composition are disclosed, for example, by U.S. Pat. Nos. 3,508,621, 3,811,507 or 3,890,239.

U.S. Pat. No. 4,077,471 discloses a surfactant mixture for use in a formation whose deposit water has a salt content of from 7 to 22%. The mixture comprises a water-soluble alkylpolyalkoxyalkyl sulfonate or alkylarylpolyalkoxyalkyl sulfonate, and a water-insoluble nonionic surfactant composed of an ethoxylated aliphatic alcohol or an ethoxylated alkyl-substituted aromatic alcohol.

EP 003 183 B1 discloses surfactants of the general formula R—O-polypropoxy-polyethoxy-X, where X is a sulfate, sulfonate, phosphate or carboxylic acid group. In a preferred embodiment of the invention, R may be a branched alkyl radical having from 10 to 16 carbon atoms, for example an isotridecyl radical.

To prepare polyether sulfonates, it is possible to proceed from corresponding alkyl alkoxylates whose terminal OH groups are utilized in further reaction steps in order to provide the alkyl alkoxylates with a terminal sulfonic acid group. To this end, it is possible in a known manner to substitute the terminal OH group of the alkyl alkoxylate with a suitable leaving group, for example by reaction $SOCl_2$, $PCl_3$ or $COCl_2$, which substitutes OH for Cl. In a second step, the chlorine atom can be replaced nucleophilically with —$SO_3H$ by reaction with $Na_2SO_3$. This reaction presents problems especially in the case of alkyl alkoxylates with relatively large carbon radicals and relatively short alkoxy chains, because the alkyl alkoxylates are then no longer particularly water-soluble. The consequence is frequently incomplete reactions, which leads to a mixture of nonionic surfactants and anionically modified surfactants.

Alternatively, the OH group of the alkyl alkoxylate can be reacted with propane sultone, a cyclic anhydride of 3-hydroxypropanesulfonic acid. Propane sultone has the disadvantage that it is toxic and carcinogenic. In addition, reactions with sterically demanding alcohols (for example secondary alcohols) are frequently incomplete.

Moreover, as disclosed by U.S. Pat. No. 4,978,780, it is possible to add vinylsulfonic acid or a salt thereof onto the OH group of the alkyoxylate. However, vinylsulfonic acid is a comparatively expensive chemical.

It was an object of the invention to provide an improved process for preparing surfactants with a polyether sulfonate structure.

Accordingly, surfactants of the general formula (I)

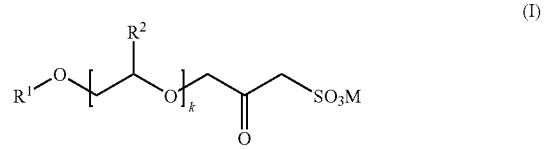

have been found, where
  $R^1$ is a straight-chain, branched, saturated or unsaturated aliphatic and/or aromatic hydrocarbon radical having from 6 to 30 carbon atoms,
  $R^2$, independently for each of the k alkoxy units, are each hydrogen or a straight-chain, branched, aliphatic or aromatic hydrocarbon radical having from 1 to 10 carbon atoms, k is from 0 to 35 and M is $H^+$ and/or an x-valent counterion $1/x\, Y^{x+}$.

Additionally found has been a process for preparing such surfactants, and their use for various purposes, including tertiary mineral oil extraction.

Figure 2:
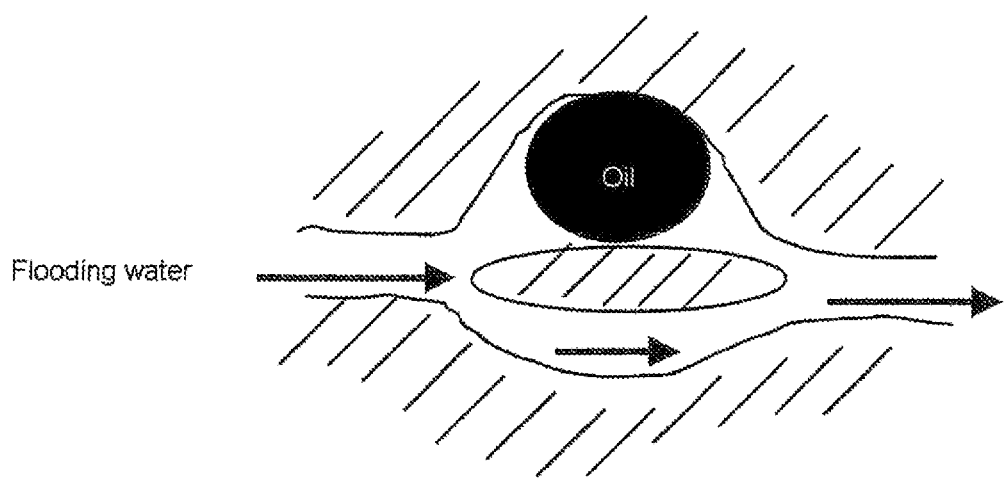

Drawings appended:

FIG. 1 Situation at the start of secondary oil extraction: completely oil-filled rock pore.

FIG. 2 Situation toward the end of secondary oil extraction: the flooding water has formed a channel and flows through the channel without picking up further oil.

Figure 3:
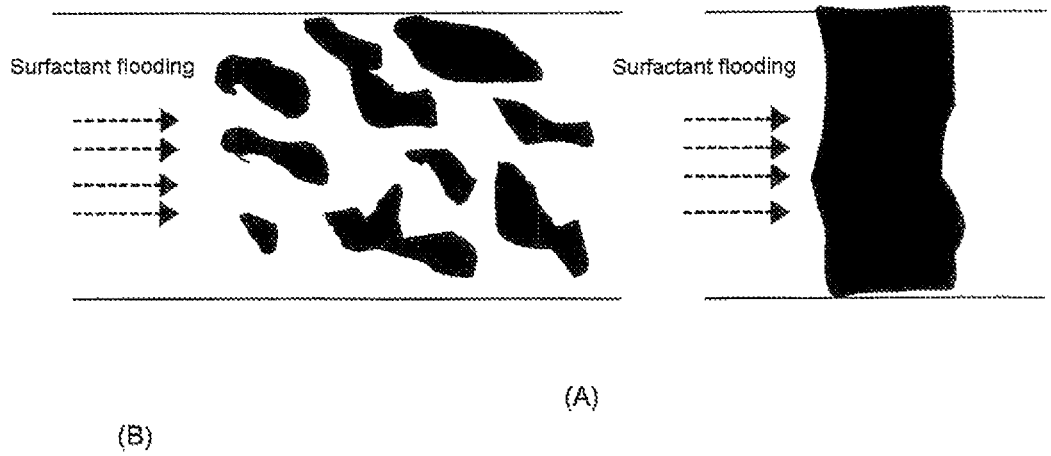

FIG. 3 Schematic illustration of surfactant flooding in a mineral oil formation: oil droplets released from the rock pores before (A) and after (B) combination to a continuous oil bank.

Figure 4:
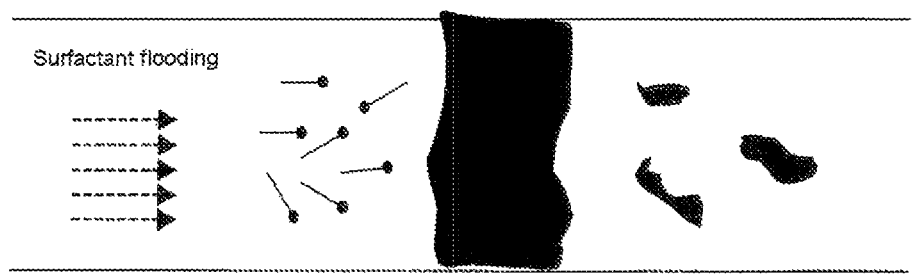

FIG. 4 Schematic illustration of the progress of the continuous oil bank in the mineral oil formation. The oil bank absorbs new oil droplets in flow direction. Surfactant is released counter to the flow direction.

Regarding the invention, the following should be stated specifically:

The inventive surfactants have the general formula

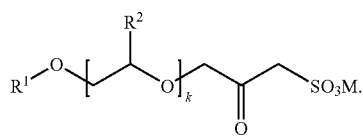

(I)

The inventive surfactants (I) consist of a hydrocarbon radical $R^1$, a polyoxyalkylene group composed of k alkoxy units, where the k alkoxy units may be the same or different and have, as a head group, a propanonylsulfonic acid group.

In the formula (I), $R^1$ is a straight-chain, branched, saturated or unsaturated, aliphatic and/or aromatic hydrocarbon radical having from 6 to 30 carbon atoms, preferably from 10 to 22 carbon atoms.

Examples of suitable $R^1$ radicals comprise especially linear or branched $C_{10}$- to $C_{22}$-alkyl radicals and linear or branched $C_{12}$- to $C_{22}$-alkenyl radicals. They are preferably linear or branched $C_{10}$- to $C_{22}$alkyl radicals, more preferably linear or branched $C_{12}$- to $C_{20}$-alkyl radicals and most preferably linear or branched $C_{16}$- to $C_{18}$-alkyl radicals. When the radicals are branched, degrees of branching of more than 0.5 are preferred.

The $R^2$ radicals are each independently H or straight-chain, branched aliphatic or aromatic hydrocarbon radicals having from 1 to 10 carbon atoms. $R^2$ is preferably H, or methyl, ethyl and/or phenyl group, and is more preferably H or methyl. In other words, the alkoxy groups are preferably ethoxy groups and/or propoxy groups. In the above formula, the representation of the alkoxy group as —$CH_2CH(R^2)O$— should exclusively also include units of the formula —$CH(R^2)CH_2O$—, i.e. the incorporation of the alkoxy group into the surfactant in inverse orientation, and it is of course also possible for both arrangements to be represented in one surfactant molecule. Preference is given to an arrangement as shown in formula (I). Preferably at least 50% of the alkoxy groups present in the surfactant are ethoxy groups.

The number k in the above formula (I) is from 0 to 35, preferably from 1 to 35, more preferably from 1 to 20 and most preferably from 2 to 15. In a known manner, it is based on the average of the alkoxy groups present in the surfactant, where the average need not of course be a natural number, but rather may also be any rational number.

In formula (I), M is $H^+$ or an x-valent counterion $1/x\, Y^{x+}$. x here is the charge of the counterion. It is preferably a monovalent counterion such as $NH_4^+$, ammonium ions with organic radicals or alkali metal ions. Y is preferably $Li^+$, $Na^+$ and $K^+$, and more preferably $Na^+$. The alkyl ether sulfonate may thus be present as a free acid or as a salt thereof.

In a preferred embodiment of the invention, the inventive surfactants are those of the general formula (II)

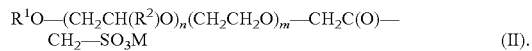

(II).

The number n here represents values from 0 to 15, preferably from 0 to 7 and more preferably from 0 to 5, and m represents values from 0 to 20, preferably from 1 to 20, more preferably from 2 to 15, where the sum of n and m in each case gives the value k defined above. Preferably, m>n, i.e., in the preferred variant, the number of ethoxy groups is greater than that of alkoxy groups.

The arrangement of alkoxy groups and ethoxy groups in the inventive surfactant—where both types of groups are present—may be random or alternating, or a block structure may be present. It is preferably a block structure in which the alkoxy and ethoxy groups are actually arranged in the $R^1O$-alkoxy block—ethoxy block-$CH_2C(O)$—$CH_2$—$SO_3M$ sequence.

The inventive surfactants can be prepared in a three-stage synthesis, wherein, in a first synthesis stage, an alkyl alkoxylate of the general formula (III) is prepared.

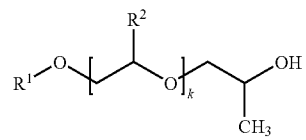

(III)

The alkyl alkoxylates (III) can be prepared in a manner known in principle by alkoxylating an alcohol $R^1$—OH with alkylene oxides

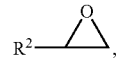

, wherein the alkoxylation is ended using propylene oxide, so as to obtain an alkyl alkoxylate with the terminal —$CH_2CH(CH_3)$—OH group shown in formula (III).

The alcohols $R^1$—OH are selected correspondingly in the surfactant according to the desired hydrophobic $R^1$ radical. Examples of suitable alcohols comprise pentadecanol, hexadecanol, heptadecanol, octadecanol, nonadecanol or eicosanol. They may in each case be 1-alkanols, or else alkanols in which the OH group is not arranged in the 1 position. The alcohols may be straight-chain or else branched. They may, for example, be fatty alcohols or preferably alcohols which can be obtained by hydroformylating olefins. The latter are also known as oxo alcohols. For the synthesis, it is of course possible not only to use pure alcohols but also typical technical mixtures of different alcohols.

In this case, the alkoxylation is performed in accordance with the invention in such a way that the alcohol is first reacted—according to the desired properties of the surfactant—with any alkylene oxides. After the consumption of all or at least of the majority of the alkylene oxides used, at least 1 mol of propylene oxide per mole of alcohol is once again added to complete the alkoxylation, in order to obtain a product terminated with —CH$_2$CH(CH$_3$)—OH— units. The alkoxylation is thus effected with a total of k+1 mol of alkylene oxide per mole of alcohol. Since the alkoxylation proceeds randomly, it is advisable to use the propylene oxide at least in a slight excess in order to obtain a product terminated fully with —CH$_2$CH(CH$_3$)—OH— units.

The alkoxylation can in principle be undertaken by methods known to those skilled in the art using known alkoxylation catalysts, with the proviso that the alkoxylation is undertaken such that the terminal propylene oxide group is actually incorporated predominantly in the —CH$_2$CH(CH$_3$)—OH orientation and not in the reverse orientation as —CH(CH$_3$)—CH$_2$OH. It is known to those skilled in the art that the orientation of alkylene oxide groups can be influenced by the selection of the alkoxylation catalyst. For example, basic catalysis or catalysis by DMC catalysts leads very predominantly to the incorporation of the alkoxy groups in —CH$_2$CH(CH$_3$)—OH— orientation, while acidic catalysis has the consequence of significant proportions of units with —CH(CH$_3$)—CH$_2$OH— orientation.

In the base-catalyzed alkoxylation, the alcohol R$^1$—OH can be admixed in a pressure reactor with alkali metal hydroxides, preferably potassium hydroxide, or with alkali metal alkoxides, for example sodium methoxide. It is possible by means of reduced pressure (e.g. <100 mbar) and/or increasing the temperature (30 to 150° C.) to draw off water still present in the mixture. The alcohol is then present in the form of the corresponding alkoxide. Subsequently, inert gas (e.g. nitrogen) is used for inertization, and the alkylene oxide(s) is/are added stepwise at temperatures of from 60 to 180° C. up to a pressure of max. 10 bar, with the proviso that the addition of the alkylene oxides is ended with the addition of at least one mole of propylene oxide per mole of alcohol, such that the synthesized alkyl alkoxylate has a —CH$_2$CH(CH$_3$)—OH— group as the terminal group. Thereafter, the catalyst can be neutralized by adding acid (e.g. acetic acid or phosphoric acid) and can be filtered off if required. Alkyl alkoxylates prepared by means of KOH catalysis generally have a relatively wide molecular weight distribution.

In a preferred embodiment of the invention, the alkyl alkoxylates (III) are synthesized by means of techniques known to those skilled in the art, which lead to narrower molecular weight distributions than in base-catalyzed synthesis. To this end, the catalyst used may, for example, be double hydroxide clays, as described in DE 43 25 237 A1. The alkoxylation can more preferably be effected using double metal cyanide catalysts (DMC catalysts). Suitable DMC catalysts are disclosed, for example, in DE 102 43 361 A1, especially paragraphs [0029] to [0041], and the literature cited therein. For example, catalysts of the Zn—Co type can be used. To perform the reaction, the alcohol R$^1$—OH can be admixed with the catalyst and the mixture can be dewatered as described above and reacted with the alkylene oxides as described. Owing to its small amounts, the catalyst can remain in the product. Inventive surfactants prepared by means of DMC catalysis are notable in that they result in better lowering of the interface tension in the water-mineral oil system than products prepared by means of KOH catalysis.

It is of course also possible to conduct the synthesis in two stages by initially acid-catalyzing the alkoxylation and switching to basic catalysis no later than before addition of the last mole of propylene oxide.

In a further synthesis step, the alkyl alkoxylate (III) is oxidized to the alkyl alkoxylate (IV) which has an acetonyl group as the terminal group.

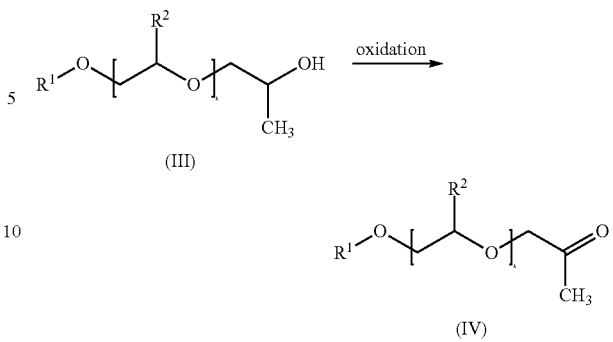

The oxidation can be undertaken by means of methods known to those skilled in the art, for example by oxidation with H$_2$O$_2$ and a transition metal catalyst, or by oxidation with O$_2$ using a suitable catalyst, for example Pd/C.

In general, the conversion in this stage is more than 90%.

The acetonyl-terminated alkyl alkoxylate (IV) formed can finally be reacted with SO$_3$ or another SO$_3$ source, for example oleum or Cl—SO$_3$H, to give the inventive surfactant (I).

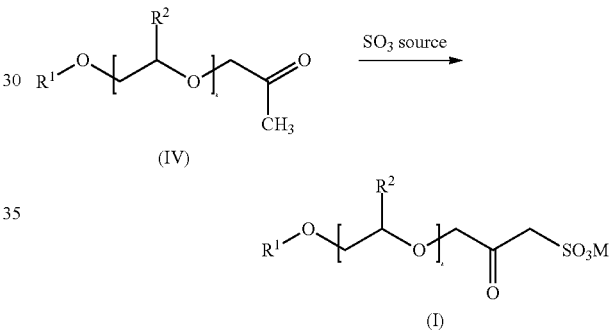

The reaction can be carried out, for example, by the methods described by U.S. Pat. Nos. 4,987,249, 5,430,180 or W. Grot, J. Org. Chem. 30 (1965), 515-517. In general, the conversion in this stage too is more than 90%. After the sulfonation has been performed, the reaction mixture can be neutralized with a base, for example NaOH or KOH.

The inventive surfactants (I) can in principle be used in all applications in which alkyl polyether sulfonates are customarily used as surfactants. By virtue of appropriate selection of R$^1$ and length and type of the alkoxy group, it is possible to adjust the properties of the inventive surfactants (I) to the particular application in a simple manner. They can, for example, be used in washing and cleaning compositions, in ore extraction, in metal processing, in textile production, in leather processing, in emulsion stabilization or in the formulation of crop protectants.

In a preferred embodiment of the invention, the inventive surfactants are used for tertiary mineral oil extraction. By lowering the interface tension between oil and water to a high degree, they bring about, particularly good mobilization of the crude oil in the mineral oil formation.

To this end, they are injected into the mineral oil deposit through at least one injection bore in the form of a suitable formulation, and crude oil or a crude oil-water emulsion is withdrawn from the deposit through at least one production bore. In general, a deposit is provided with several injection bores and with several production bores. After the injection of the surfactant formulation, the so-called "surfactant flooding", the pressure can be maintained by injecting water into the formation ("water flooding"), or preferably a higher-viscosity aqueous solution of a polymer with high thickening action ("polymer flooding"). However, techniques in which the surfactants are first allowed to act on the formation are also known. The person skilled in the art is aware of details of the technical performance of "surfactant flooding", "water flooding" and "polymer flooding", and employs an appropriate technique according to the type of deposit.

The inventive surfactants can be used for surfactant flooding preferably in aqueous formulation. In addition to water, the formulations, as a solvent, may optionally comprise not more than 50% by weight, preferably not more than 20% by weight, of water-miscible alcohols.

For tertiary mineral oil extraction, it is possible in each case to use only one of the inventive surfactants (I). However, preference is given to using a formulation which comprises at least one inventive surfactant (I) and at least one further surfactant.

The inventive surfactants can be used in this case as surfactants or else as cosurfactants. "Cosurfactant", also referred to as "secondary surfactant", is understood to mean, in a manner known in principle, a surfactant which is added in a relatively small amount to other surfactants or surfactant mixtures in order to improve their property profile. The amount of all inventive surfactants (I) together, based on the total amount of all surfactants used in a surfactant mixture, is determined by the person skilled in the art according to the type of properties desired. The amount of inventive surfactants (I) is generally from 1 to 99% by weight based on the total amount of all surfactants in the mixture. The amount is preferably from 10 to 95% by weight.

Examples of further surfactants which can be used as well as the surfactants (I) comprise anionic surfactants, especially organic sulfonates, for example olefinsulfonates or alkylarylsulfonates, nonionic surfactants or anionic surfactants which are prepared by anionic modification of nonionic surfactants, for example ether sulfates, ether sulfonates or ether carboxylates, or alkylpolyols and/or alkylpolyglucosides. It is additionally possible to use cationic and/or betainic surfactants.

In addition to the surfactants, the formulations may also comprise further components, for example $C_1$- to $C_8$-alcohols and/or basic salts (so-called "alkali surfactant flooding"). Such additives can be used, for example, to reduce retention in the formation.

Mixtures which are preferred for tertiary mineral oil extraction and comprise inventive surfactants (I) are described below.

In a preferred embodiment of the invention, a mixture (M) of at least one inventive surfactant (I) (also referred to hereinafter as M1) and at least one anionic surfactant (M2) can be used for tertiary mineral oil extraction. Such mixtures are particularly suitable for use in high-salinity deposits. For use, the mixtures can be formulated as described above, preferably with suitable solvents or mixtures of solvents.

Suitable components (M2) in addition to the inventive surfactants (M1) are particularly nonionic surfactants of the general formula (V)

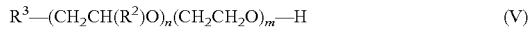

$$R^3-(CH_2CH(R^2)O)_n(CH_2CH_2O)_m-H \quad (V)$$

where the indices n and m and also $R^2$ are each as defined above, and where $R^3$ is an aliphatic or araliphatic $C_{10}$- to $C_{20}$-hydrocarbon radical, preferably an aliphatic and/or aromatic $C_{14}$- to $C_{18}$-hydrocarbon radical. The hydrocarbon radicals may, for example, be 4-dodecylphenyl radicals, or hexadecyl, heptadecyl or octadecyl radicals.

Also preferred are mixtures of at least one surfactant (M1') with ionic behavior and at least one surfactant (M2') with nonionic behavior, at least one of the surfactants (M1') or (M2') being an inventive surfactant (I). "Surfactants with ionic behavior" and "surfactants with nonionic behavior" are in each case understood to mean surfactants in which the head group comprises both ionic and nonionic structural units, and in which, according to the chemical structure and/or use conditions, nonionic behavior or ionic behavior dominates. A typical nonionic surfactant with polyether units behaves more hydrophobically with increasing temperature in an oil-water-surfactant system. Such surfactants initially form an oil-in-water emulsion at relatively low temperatures, i.e. an emulsion of oil in a continuous water phase. As the temperature increases, there is finally a phase transition to a water-in-oil emulsion, i.e. an emulsion of water in a continuous oil phase. This transition can be monitored, for example by a conductivity meter. The transition from a continuous water phase to a discontinuous water phase is associated with a significant decline in the conductivity. Surfactants with ionic behavior have the reverse behavior and become more hydrophilic with increasing temperature. A water-in-oil emulsion is thus converted with increasing temperature to an oil-in-water emulsion, which can likewise be monitored efficiently by a conductivity meter.

In a further preferred embodiment, the mixture (M), as well as components (M1) and (M2), also comprises a polymeric cosurfactant (M3). The amount of the cosurfactant (M3) is not more than 49.9% by weight based on the total amount of all surfactants (M1), (M2) and (M3) used. The amount is preferably from 1 to 10% by weight. It is advantageously possible with such polymeric cosurfactants to reduce the amount of surfactant needed to form a microemulsion. Such polymeric cosurfactants are therefore also referred to as "microemulsion boosters".

The polymeric cosurfactants (M3) are amphiphilic block copolymers which comprise at least one hydrophilic block and at least one hydrophobic block. They preferably have molecular masses $M_n$ of from 1000 to 50 000 g/mol. The hydrophilic blocks and the hydrophobic blocks should generally have at least a molar mass of in each case 500 g/mol, preferably 750 g/mol and more preferably 1000 g/mol. The hydrophobic and hydrophilic blocks may be linked to one another in various ways. The polymers may, for example, be diblock copolymers or multiblock copolymers, in which the hydrophobic and hydrophilic blocks are arranged in alternation. The polymeric cosurfactants (M3) may be linear, branched or star-shaped, or they may be comb polymers which have a main chain and one or more side chains bonded to it.

Preference is given to block copolymers which, as hydrophilic blocks, have polyethylene oxide blocks or random polyethylene oxide-polypropylene oxide blocks, where the propylene oxide content should not exceed 40 mol %, preferably 20 mol % and more preferably 10 mol % based on the sum of the ethylene oxide and propylene oxide units polymerized into the block. The blocks are preferably pure polyethylene oxide blocks. The hydrophobic blocks may, for example, be blocks of polypropylene oxide or $C_4$- to $C_{12}$-alkylene oxides. In addition, hydrophobic blocks may be formed, for example, from hydrocarbon units or (meth) acrylic esters.

Preferred polymeric cosurfactants (M3) comprise polypropylene oxide-polyethylene oxide block copolymers, polyisobutene-polyethylene oxide block copolymers and comb polymers with polyethylene oxide side chains and a hydrophobic main chain, where the main chain comprises preferably essentially olefins or (meth)acrylates as structural units. The term "polyethylene oxide" here shall in each case include polyethylene oxide blocks comprising propylene oxide units according to the above definition. Further details regarding the preferred polymeric cosurfactants (M3) are disclosed in WO 2006/131541.

The invention claimed is:

1. A surfactant of the general formula (I)

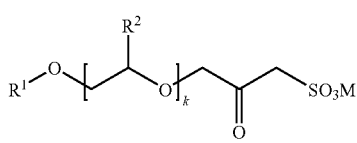

(I)

where
R$^1$ is a straight-chain, branched, saturated or unsaturated aliphatic and/or aromatic hydrocarbon radical having from 6 to 30 carbon atoms,
R$^2$, independently for each of the k alkoxy units, are each hydrogen or a straight-chain, branched, aliphatic or aromatic hydrocarbon radical having from 1 to 10 carbon atoms,
k is from 0 to 35 and
M is H$^+$ and/or an x-valent counterion 1/x Y$^{x+}$.

2. A surfactant according to claim 1, wherein k is from 1 to 20.

3. A surfactant according to claim 1, wherein R$^2$ is hydrogen or methyl.

4. A surfactant according to claim 1, wherein R$^1$ comprises linear or branched C$_{10}$- to C$_{22}$-alkyl radicals.

5. A surfactant according to claim 2, wherein R$^2$ is hydrogen or methyl.

6. A surfactant according to claim 2, wherein R$^1$ comprises linear or branched C$_{10}$- to C$_{22}$-alkyl radicals.

7. A surfactant according to claim 3, wherein R$^1$ comprises linear or branched C$_{10}$- to C$_{22}$-alkyl radicals.

8. A surfactant mixture (M) comprising at least two different surfactants (M1) and (M2), wherein at least one of the surfactants is a surfactant (I) according to claim 1.

9. The surfactant mixture (M) according to claim 8, wherein (M1) is the surfactant (I) and (M2) is at least one nonionic surfactant.

10. The surfactant mixture (M) according to claim 8, which comprises at least one surfactant (M1') with ionic behavior and at least one surfactant (M2') with nonionic behavior.

11. The surfactant mixture (M) according to claim 8, which additionally comprises up to 49.9% by weight, based on the sum of all surfactants in the mixture, of at least one polymeric cosurfactant (M3).

12. The surfactant mixture (M) according to claim 11, wherein the polymeric cosurfactant (M3) is a block copolymer which comprises at least one hydrophobic block and at least one hydrophilic block.

13. The surfactant mixture (M) according to claim 12, wherein (M3) is a polymer selected from the group of polypropylene oxide-polyethylene oxide block copolymers, polyisobutene-polyethylene oxide block copolymers and comb polymers with polyethylene oxide side chains and a hydrophobic main chain.

14. A process for preparing surfactants according to claim 1, comprising:
alkoxylating an alcohol of the general formula R$^1$—OH with k+1 mol of alkylene oxides

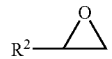

per mole of alcohol to give the alkyl alkoxylate (III)

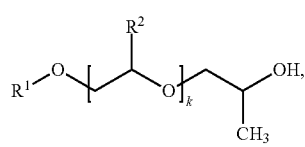

(III)

the alkoxylation being performed in such a way that at least 1 mol of propylene oxide is used per mole of alcohol toward the end of the alkoxylation,
oxidizing the alkyl alkoxylate (III) by means of a suitable oxidizing agent to give an ω-acetonylalkyl alkoxylate (IV)

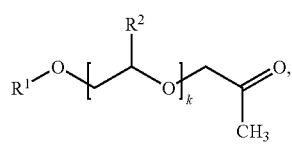

(IV)

and
reacting the ω-acetonylalkyl alkoxylate (IV) with a sulfonating agent to give the surfactant (I)

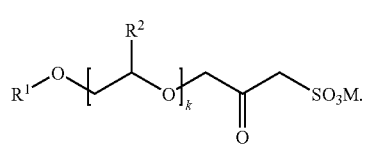

(I)

15. The process according to claim 14, wherein the sulfonating agent used is one selected from the group of SO$_3$, oleum and chlorosulfonic acid.

16. A process for preparing surfactants according to claim 2, comprising:
alkoxylating an alcohol of the general formula R$^1$—OH with k+1 mol of alkylene oxides

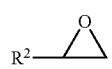

per mole of alcohol to give the alkyl alkoxylate (III)

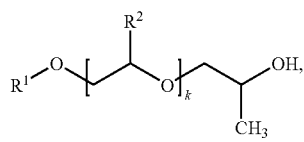
(III)

the alkoxylation being performed in such a way that at least 1 mol of propylene oxide is used per mole of alcohol toward the end of the alkoxylation, oxidizing the alkyl alkoxylate (III) by means of a suitable oxidizing agent to give an ω-acetonylalkyl alkoxylate (IV)

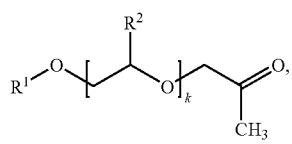
(IV)

and reacting the ω-acetonylalkyl alkoxylate (IV) with a sulfonating agent to give the surfactant (I)

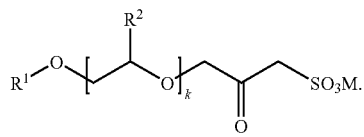
(I)

17. A process for preparing surfactants according to claim 3, comprising:
alkoxylating an alcohol of the general formula $R^1$—OH with k+1 mol of alkylene oxides

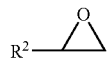

per mole of alcohol to give the alkyl alkoxylate (III)

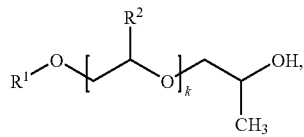
(III)

the alkoxylation being performed in such a way that at least 1 mol of propylene oxide is used per mole of alcohol toward the end of the alkoxylation, oxidizing the alkyl alkoxylate (III) by means of a suitable oxidizing agent to give an ω-acetonylalkyl alkoxylate (IV)

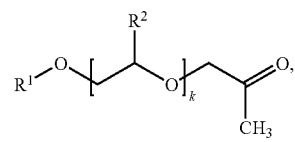
(IV)

and reacting the ω-acetonylalkyl alkoxylate (IV) with a sulfonating agent to give the surfactant (I)

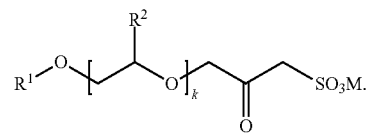
(I)

18. A washing and cleaning composition which comprises the surfactant according to claim 1.

19. A formulation for crop protectants which comprises the surfactant according to claim 1.

20. A process for ore extraction which comprises utilizing the surfactant according to claim 1.

21. A method for processing metal which comprises utilizing the surfactant according to claim 1.

22. A process for producing textiles which comprises utilizing the surfactant according to claim 1.

23. A process for producing leather which comprises utilizing the surfactant according to claim 1.

24. A process for stabilizing an emulsion which comprises utilizing the surfactant according to claim 1.

25. A process for tertiary mineral oil extraction which comprises utilizing the surfactant according to claim 1.

26. A process for tertiary mineral oil extraction which comprises utilizing the surfactant mixture according to claim 8.

* * * * *